United States Patent [19]

Darby et al.

[11] Patent Number: 5,370,133
[45] Date of Patent: Dec. 6, 1994

[54] LOWER LEG, ANKLE AND FOOT IMMOBILIZATION BRACE WITH UNIFORM, ADJUSTABLE COMPRESSION

[75] Inventors: H. Darrel Darby; H. Darrel Darby, II, both of Huntington, W. Va.

[73] Assignee: Darco International, Inc., Huntington, W. Va.

[21] Appl. No.: 199,873

[22] Filed: Feb. 22, 1994

[51] Int. Cl.⁵ ........................ A61F 5/37; A61F 5/00
[52] U.S. Cl. ............................ 128/882; 602/23; 602/27
[58] Field of Search ............... 128/882, 878, 879, 880, 128/881; 602/4, 5, 6, 20, 21, 22, 23, 27

[56] References Cited

U.S. PATENT DOCUMENTS

| | | | |
|---|---|---|---|
| Re. 32,680 | 5/1988 | Pompa | 128/882 |
| 3,561,139 | 2/1971 | Stillman | 36/89 |
| 4,454,871 | 6/1984 | Mann | 602/27 |
| 4,478,214 | 10/1984 | Lamont | 128/882 |
| 4,573,456 | 3/1986 | Spann | 602/27 |
| 4,730,610 | 3/1988 | Graebe | 128/882 |
| 5,217,431 | 6/1993 | Toronto | 602/27 |

*Primary Examiner*—Michael A. Brown
*Attorney, Agent, or Firm*—Sughrue, Mion, Zinn, Macpeak & Seas

[57] ABSTRACT

A semi-flexible molded polyurethane boot closed at the rear and sides and open at the front surrounds a breathable open pore foam inner liner which covers the lower leg, ankle and foot and which forms a principal element of an improved immobilization brace. The boot is fixed to a walking sole having a minimal rocker effect, and is of minimal thickness. A boot portion of the boot has a rounded heel counter and a contoured footbed. A shock absorbing foam insole within a boot portion recess pads the plantar surface of the sole. The dorsum of the boot and the boot upper are provided with ventilation ports to ventilate the leg, ankle and foot of the user through the porous open foam liner. The dorsum of the boot portion of the boot and the boot upper are provided with spaced adjustable, leverage type closures to provide adjustable general compression and focal compression to assure a proper fit of the brace and to reduce edema induced swelling throughout the leg, ankle and foot. The boot upper and boot portion may be formed of two parts hinged together, but locked to prevent fore and aft rotation of the boot upper relative to the boot portion fixed to the sole.

15 Claims, 4 Drawing Sheets

LOWER LEG, ANKLE AND FOOT IMMOBILIZATION BRACE WITH UNIFORM, ADJUSTABLE COMPRESSION

FIELD OF THE INVENTION

The present invention relates to braces employed in immobilizing the foot and ankle as a substitute for a rigid cast, and more particularly to an improved short leg walker which provides uniform compression over the leg, foot and ankle area, which compression may be additionally focal in nature and adjustable over the totality of the walker.

BACKGROUND OF THE INVENTION

Short leg walkers are generally formed with a rigid, rocker sole designed to allow the patient or user to roll through a gait cycle while immobilizing the ankle and the foot and without bending of the foot at the metatarso-phalangeal joint. Typically, two stabilizer bars are attached to the sole on respective sides of the ankle and extend up the sides of a leg approximately three quarters of the way up the calf. The lower leg and foot are wrapped in a foam liner which closes along the front of the shin and top of the foot and which fits in between the two stabilizer bars. Typically, three VELCRO ® type hook and loop form fastener straps are wrapped around the lower leg enclosed in the foam liner and around the stabilizer bars to prevent the leg from bending at the ankle. Such hook and loop type fastener straps are also used to provide compression to the lower leg. One or two additional hook and loop type fastener straps are generally employed across the dorsum of the foot to hold the foot firmly against the inner sole of the walker. Such short leg walkers are most often used in lieu of a cast when there has been severe trauma or surgery to the ankle or foot, with the immobilization and compression of the lower leg, foot and ankle enhancing the healing process.

In such prior art short leg walkers, the stabilizer bars or stirrups are rigid, flat rods connected at their lower ends to the sole of the walker and extend to opposite sides of the leg. Such stirrups are generally of two different heights, a taller style that extends to just below the fibular neck, and a shorter style that extends approximately 4 to 6 inches above the ankle. There is usually a space between the stirrups and the medial and lateral malleolus to prevent friction. This space prevents the necessary compression of the short leg walker around the ankles, and more particularly in the Achilles triangle and distal to the malleoli. Since injuries, surgeries, etc. involving the ankle produce edema in the area, it is vital to have focal compression in the area to minimize edema.

In the past, plaster or fiberglass casts have been recognized as the ideal structure in initially dealing with these injuries. However, after the first few days, the edema subsides and the cast becomes loose on the leg, ankle and foot, no longer providing the necessary compression and rendering the cast uncomfortable while lacking the immobilization necessary for proper healing of the involved tissue.

In the prior short leg walkers, the rocker sole design used in most such walkers poses several problems for the wearer. A true rocker sole must be of sufficient thickness (height) so that an uninterrupted roll is possible through the complete gait cycle. This extra height produces a leg length discrepancy with the unaffected limb that places undue pressure on the knee, hip and lower back of the user. In those cases where arthritic charges are present, the discomfort is even more pronounced.

A second problem with the rocker sole design short leg walker is that the rocker sole is unstable when the wearer is in a stationary or standing position and movement is unnecessary and uncomfortable. Because there are no flat portions on a rocker sole, there are no natural resting points for the leg, ankle and foot encased in the short length leg walker. When the wearer is standing in a rocker sole, the wearer most often rolls back on the heel, creating pressure on the knee and hip and slight hyperextension of the knee. Where the shoe portion of the brace has no heel counter, additional instability at the sub-talar and mid-tarsal areas of the foot is created.

In such prior art short length leg walkers, the double post design utilizing the multiple VELCRO ® opposite type hook and loop fastener straps is intended to provide stabilization of the ankle and also provide compression to help reduce the edema associated with foot and ankle trauma. The area where compression is most needed lies in the Achilles triangle located behind the malleoli (ankle bone) as well as underneath and in front of the malleoli. The hook and loop type fastener straps do provide some compression, but instead of acceptable general compression, the compression more often takes the form of bands of localized pressure directly underneath the strap or straps themselves. Further, the two posts that aid in stabilization of the leg and ankle exacerbate this problem because they are designed to be the thickest over the ankle and for that reason do not conform at all to the lower leg and ankle where compression is most needed.

It is therefore a primary object of the present invention to eliminate the problems above commonly associated with known short leg walkers and to provide a more viable option to casting the lower leg when subject to surgery and trauma.

It is also a principal object of this invention to provide a lower leg, ankle and foot brace constituting an improved short leg walker which provides immobilization characterized by uniform, adjustable compression, which prevents torsion of the leg, ankle and foot as well as dorsiflexion and plantar flexion at the ankle joint, to further restrict motion at the metatarso-phalangeal joint, thereby immobilizing the ankle and foot joints and at the same time providing a shoe or boot type enclosure for greater wearer comfort and stability.

Other advantages of the present invention will become apparent from the description of the preferred embodiments and from the accompanying drawings.

SUMMARY OF THE INVENTION

The invention is directed to a lower leg, ankle and foot immobilization brace, preferably in the form of a short length leg walker incorporating a single-part or two-part semi-flexible polyurethane or other injection-molded plastic material boot to provide controlled, uniform compression of the foot, ankle and leg covered by the brace while at the same time immobilizing those aspects of the human body lower limb subject to surgery or trauma. The present invention employs a walking sole with minimal rocker effect to provide a more stable weight bearing surface and to reduce the bulk required in a true walker sole such that the sole is of similar thickness to a conventional shoe sole worn by the wearer on the non-effected foot. The boot portion of the brace is contoured much like conventional footwear with a rounded heel counter and contoured recessed footbed providing a better fit with greater stability and comfort to the wearer. The immobilization brace or short leg walker is characterized by a shock absorbing foam insole used to pad the plantar surface of the foot within the boot portion recess and to provide increased comfort to user or wearer and protection to the same. The short leg walker provides sufficient space to insert a heat or pressure moldable material strip placed on the inner sole of the shoe to assist in redistributing the weight of the patient along the plantar aspect of the foot. The heat and/or pressure moldable material strip acts as a total contact brace for use in the treatment of diabetic/ischemic ulcerations or other non-healing lesions of the foot. The boot portion of the brace or short leg walker is provided with adjustable, leverage-type pawl and rack closures to provide a readily manually adjustable, general compression closure. The adjustable closures can be tightened or loosened by the patient to accommodate an increase or decrease in edema on a localized basis over the frontal aspect of the dorsum, ankle and lower portion of the leg to assure proper fit of the brace over these user limb aspects under all circumstances. The upper portion of the boot is constructed of a slightly more flexible material than the lower boot portion in the two-part boot embodiment of the invention. While providing limited rigidity throughout the long axis of the boot upper, the boot allows the entire upper boot portion to be flexible enough to conform to the leg. In a second embodiment of the invention, a low top, short leg walker employs a single, unitary molded semi-rigid boot with a limited number of adjustable closures over the front portion of the boot upper and the dorsum, which provides the necessary and desired uniform compression throughout the more limited area of the leg, the ankle and the foot in a manner similar to that of the first embodiment. The adjustable closures have significant advantages over the presently employed VELCRO® hook and loop type fastener systems, which provide compression only under the area of the straps, tending to capture the edema between the respective VELCRO® fastener straps. The adjustable compression closures additionally simplify the process of the user in putting on and taking off the short leg walker. The single element and two-part boot portion of the short leg walker includes a plurality of spaced cutouts or ventilation ports for providing ventilation to the skin through the porous foam liner within which the affected leg, ankle and foot is inserted, which foam liner is breathable to facilitate the ventilation to the skin and which ports assist in reducing the overall weight of the high top or low top short length leg walker.

As a result, the improved short length leg walker of the invention is readily adjustable in terms of applied compression uniformly over the foot to compensate for either increased or decreased edema and assuring a good fit of the brace throughout the healing process. Due to past difficulties in maintaining the proper compression in the area of the malleoli, the short length leg walker of the present invention employs L-shaped or other form decompression pads which are used initially in the presence of edema to reduce fluids accumulating around the malleoli.

DESCRIPTION OF THE PREFERRED EMBODIMENTS

Figure 1:
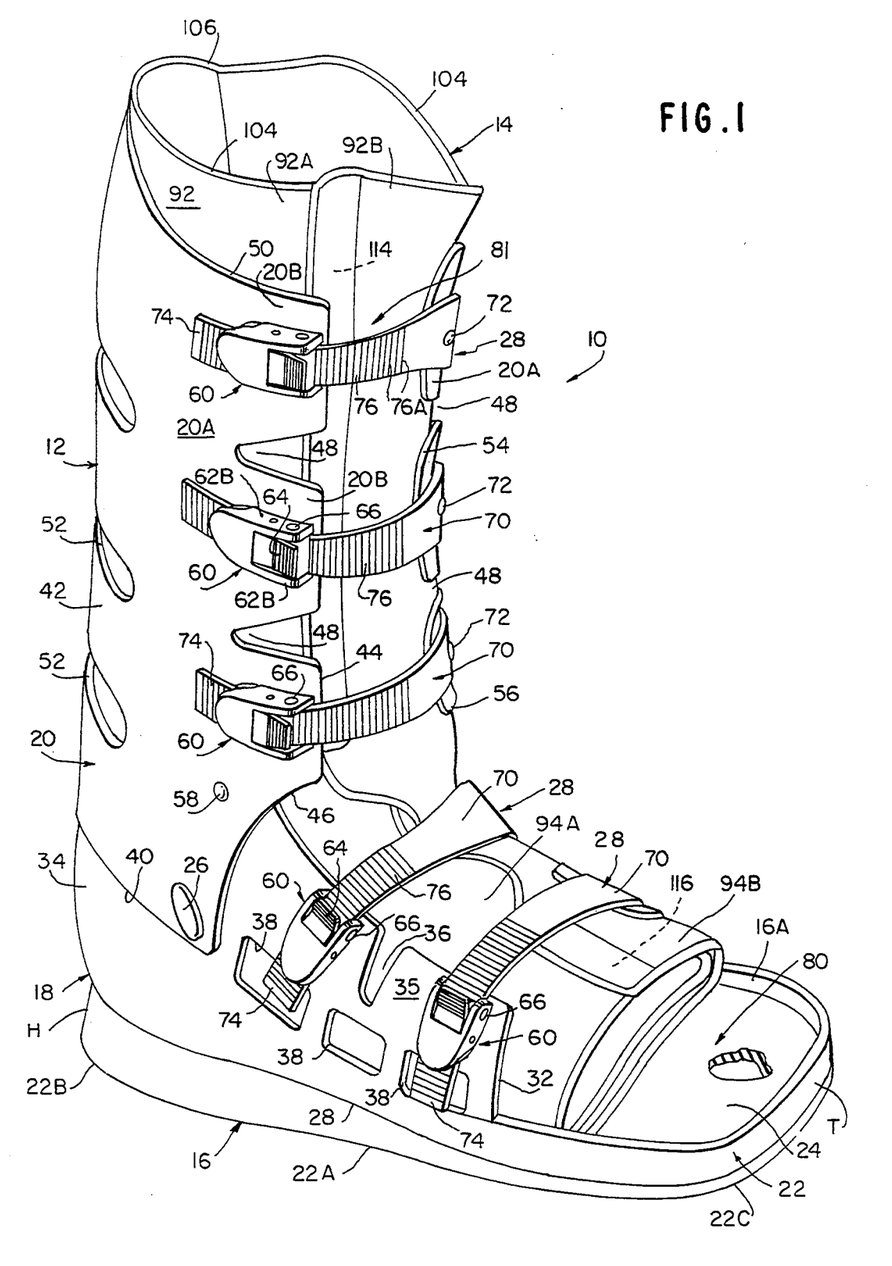
FIG. 1 is a perspective view, partially broken away of a high top, short length leg walker forming a preferred embodiment of the invention.
Figure 2:
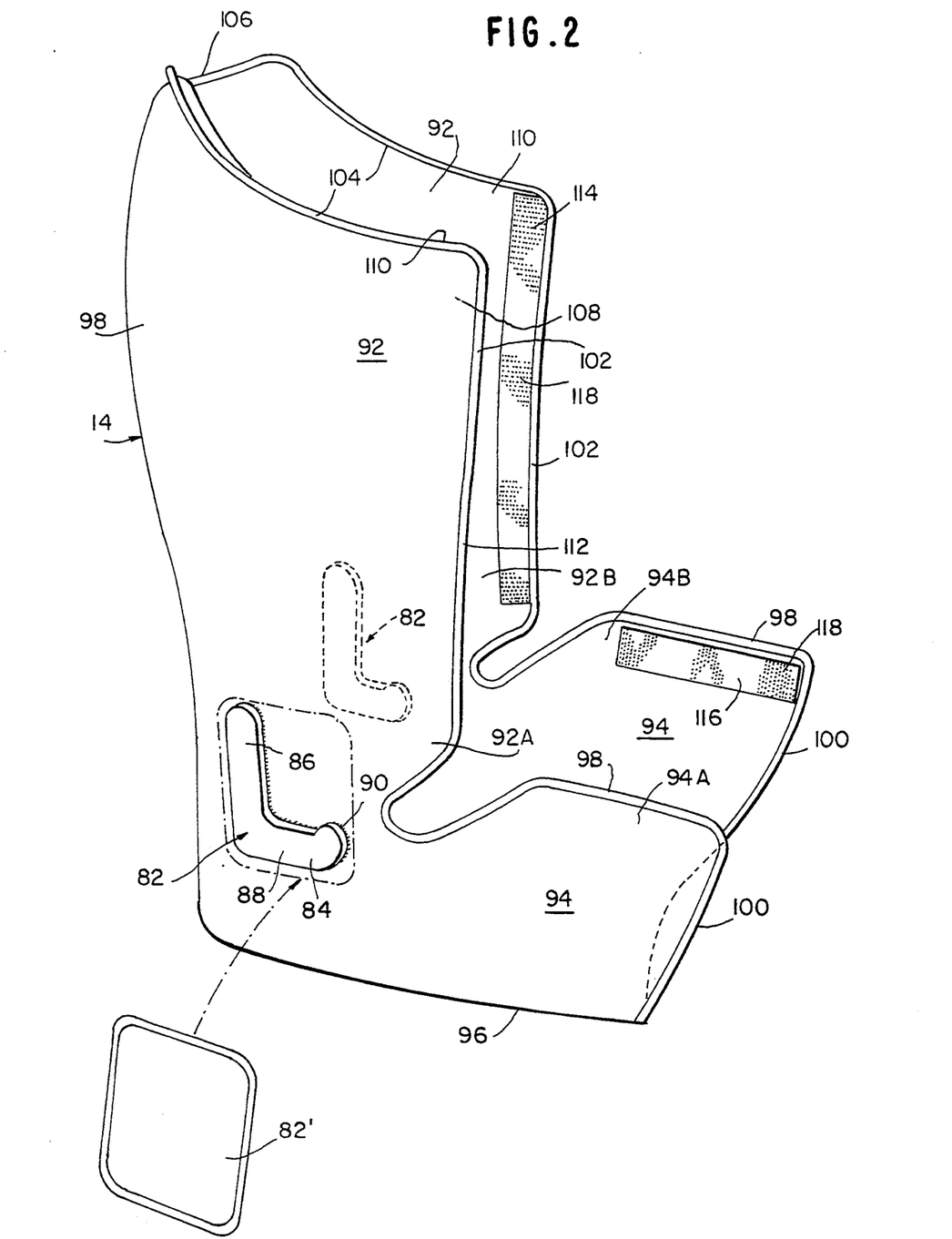
FIG. 2 is a perspective view of a removable breathable foam liner forming a principal element of the short length leg walker of FIG. 1.

Referring to FIGS. 1 and 2, a lower leg, ankle and foot, high top immobilization brace, indicated generally at 10, forms a first, preferred embodiment of the invention consisting principally of a semi-flexible boot indicated generally at 12 formed of an injection molded material such as polyurethane and surrounding and supporting an internal breathable foam lining indicated generally at 14. The brace 10 provides controlled, uniform compression of the foot, ankle and leg covered by the brace, while at the same time immobilizing these components of the body of the user or wearer. The boot 12 or outer component of the brace is provided with a walking sole indicated generally at 16, consisting of an outer sole 22 of significant thickness and having bonded thereto at the top 28 of the outer sole 22 a thinner foam insole 24. The walking sole 16 is provided with a minimal rocker effect having a relatively flat central sole bottom surface 22A terminating, at the rear or heel H of the brace, in an upwardly and rearwardly rounded bottom surface portion 22B. The sole terminates at the front or toe T in an upwardly oblique, gently rounded sole bottom surface 22C. Over its length, the upper surface 28 is preferably contoured to provide a better fit for the user's foot with good stability and comfort. The shock absorbing foam insole 24 functions to pad the plantar surface of the user's foot and to provide comfort and protection to the same. The insole may be formed of EVA foam. Further, the portion of the sole underlying the forefoot is slightly more flexible than that to the rear and in the area of the heel H. By employing a minimal rocker effect, the walking sole 16 provides a highly stable weight bearing surface and is of reduced bulk compared to a true walker sole of significantly greater thickness, having a walking sole thickness which is approximately of the same thickness as a conventional shoe or boot sole. As such, the user of the immobilization brace 10 is not subject to undue pressure on the knee, hip and lower back during ambulation, nor does the user experience instability when in a stationary or standing position, and the short leg walker 10 is comfortable before, during and after ambulation.

As may be seen from FIG. 1, the molded polyurethane walking sole 16 at the toe T has a relatively large open toe area indicated generally at 80, partially formed by a front wall of a boot portion indicated generally at 18 of the boot 12 or outer component of the brace 10. In the open toe area 80, the boot portion 18 is provided with a semi-circular vertical wall portion or lip 18A of corresponding planar configuration to that of the walking sole 16 providing significant protection to the exposed toes of the user. The lip 18A rises well above the upper surface of insole 24 which resides in the recess of the boot portion 18. The boot 12 carries above the boot portion 18, a boot upper or upper portion, indicated generally at 20, which is pivotably coupled to opposite sides of the boot portion 18 by relatively large size rivets 26 for pivoting about a horizontal axis A—A. The upper 20 rises to a height in this embodiment considerably higher than that of the boot portion 18. The boot portion 18 is contoured much like conventional footwear with a rounded heel counter 34, a recessed, contoured footbed 18B and laterally spaced sides 35. The boot portion sides 35 extend from the heel H in the direction of the toe of the immobilization brace and terminate in vertical front edges 32. The upper edge 30 of the boot portion 18 is of arcuate configuration rising from the vertical upright edge 32 towards the counter 34. The opposite sides 35 are integrally joined by counter 34 which extends about the rear of the immobilization brace. The upper edges 30 include a V-shaped notch or slot at 36 providing additional flexibility to the sides 35 of the boot portion 18 of boot 12. A series of longitudinally spaced ventilation ports or openings 38 of generally trapezoidal form are formed within the boot portion 18 to permit the ingress and egress of air for ventilation of the foot of the user. The ventilation openings or ports 38 cooperate with the breathable foam liner 14 to provide such comfort to the wearer. The boot 12 is completed by the upper 20 which is generally C-shaped in horizontal cross-sectional configuration, being vertically elongated and having a frontal opening indicated generally at 81. Preferably, the upper portion 20 of the boot 12 is constructed of slightly less rigid material than the boot portion 18 providing sufficient rigidity throughout the long axis of the upper, while being semi-flexible, allowing the entire upper portion of the boot or immobilization brace 10 to conform to the leg of the user. The boot upper 20 is of unitary molded plastic such as polyurethane and has laterally opposed arcuate sides 20A defining the elongated, frontal opening 81, the sides being joined by a rear wall 42. A plurality of arcuate ventilation openings or ports 52 are provided within the rear wall 42 which add flexibility to the boot upper 20 and perform the same function as the trapezoidal ventilation ports or openings 38 within the boot portion 18 of the boot 12. The ventilation ports 52 are three in number in the illustrated embodiment of FIG. 1. The boot upper 20 terminates at the bottom, in a lower, near horizontal edge 40, and from the front end of each side 20A, there rises a forwardly and upwardly arcuate edge 46 terminating in a vertical edge 44. Edges 44 rise to an arcuate edge 50 at the top of the upper, extending rearwardly and upwardly to join opposite sides 20A of the upper. A pair of V-shaped notches are formed at 48 within both front edges 44 of the upper, providing areas 20B of increased flexibility to three hinge mounting portions of the opposite sides 20A of the boot upper.

An important aspect of the invention resides in the inclusion of pawl and rack leverage closures or fasteners indicated generally at 28, which couple the opposite sides 20A of the boot upper at the three spaced areas 20B defined by the V-shaped notches 48. In similar fashion, the adjustable pawl and rack type leverage closures 28 are employed for adjustably coupling the opposite sides 35 of the boot portion 18 of the boot 12. The effect of the same is to provide a uniform or variable compression over the full extent of the boot 12 from the lower leg through the ankle and across the dorsum of the user, protected and enveloped by the breathable porous liner 14, which will be described in detail hereinafter.

All of the leverage closures 28 are identical and comprised principally of a flexible molded plastic strap indicated generally at 70 and a pivoted buckle indicated generally at 60, which may be respectively mounted to the opposite sides 20A of the boot upper 20, and opposite sides 35 of the boot portion 18 of boot 12. In FIG. 1, the buckle 60 of leverage closure or fastener 28 of the boot upper 20 is mounted by way of a rivet 68 to the side 20A of the boot upper centered within an intermediate boot upper portion or area 20B defined by upper and lower V-shaped notches 48. The buckle 60 includes a U-shaped hinge plate 62 having a base 62A and upper and lower, horizontal right angle flanges through which extend a hinge pin or pivot pin 66 and to which is mounted for pivoting about the axis of the pivot pin 66 one end of a closure lever 59 which in turn pivotably mounts a L-shaped pawl 64 having a right angle flange extending across and at right angles to the longitudinal axis of strap 70. The flange is capable of engaging within the grooves defined by teeth of a rack 76 on the exterior, serrated face of the strap 70. Coupling is effected between the serrated or rack surface portion of strap 70 and the L-shaped pivotable pawl 64 of buckle 60 by insertion of the free end 74 of the strap 70 beneath the L-shaped, spring-biased pawl 64 and within a throat of buckle 62 defined by pawl 64 and an underlying guide plate 69 and forcing the strap to project within the buckle to a greater or lesser extent.

Figure 3:
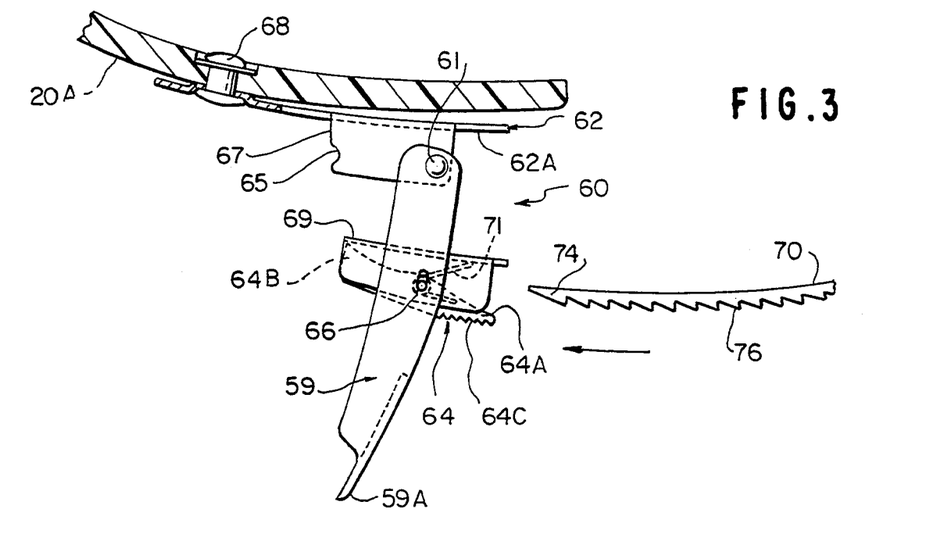
FIG. 3 is a top plan view of a buckle and strap of a levered closure having a lever pivoted at right angles a mounting bracket to illustrate the entry slot for a serrated strap.
Figure 4:
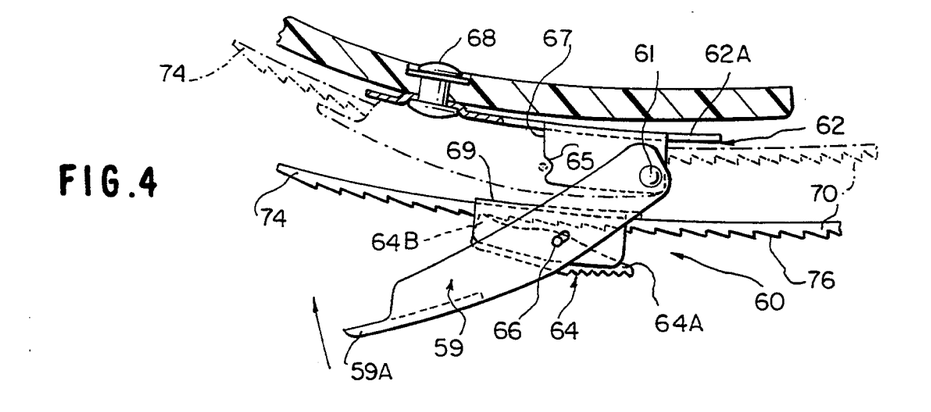
FIG. 4 is a similar plan view with the pivotable lever rotated approximately 60° clockwise from that of FIG. 3 and with the free end of the serrated strap inserted beneath the spring biased pivotable pawl.

The leverage closure or fastener 28 functions to initially receive the free end of the serrated strap 70 between a U-shaped strap guide plate 69 pivotably mounted to bifurcated arms 59B of a lever 59, which arms 59B, remote from a gripping tab 59A of the lever, are pivoted to sidewalls or flanges 62B of a U-shaped lever mounting plate or bracket 62 by rivets 61. In turn, the base 62A of the lever mounting plate or bracket is pivotably mounted by rivet 68 at a rear end thereof to a side of either upper 20 or the boot portion 18 of the boot 12. A pair of rivets 61 provide a pivot axis A connection between respective arms 59B of the lever 59 and the sidewalls 62B of the mounting plate or bracket 62. Rear edges 67 of the lever mounting plate flanges or sidewalls 62B carry aligned locking notches 65 of U-shape for a pawl pivot pin 65, which commonly pivotably mounts both the pawl 64 and the U-shaped strap guide plate 69 to lever 59 for pivoting about pivot axis B. A coil spring 71 is wound about one end of the pivot pin 65, with opposite ends of the coil spring abutting the interior faces of the opposed pawl 64 and the U-shaped strap guide 69. The bias of the coil spring 71 biases the right angle gripping flange 64B of the pawl 64 in contact with the facing surface of the U-shaped strap guide plate 71. The right angle gripping flange 64B projects from the base 64A of the pawl 64, with the pawl being pivoted intermediate of the gripping flange and a serrated friction surface 64C of the pawl base 64A. By pressing on the serrated friction surface 64C of the pawl base 64A, the gripping flange 64B is raised from the surface of the U-shaped strap guide plate 69, permitting the free end 74 of the serrated strap 70 to freely pass over the interior surface of the U-shaped strap guide plate 69 within a throat 60 thereof, past the raised gripping flange 64B of the pawl 64. The insertion of the free end 74 of the strap 70 is effected with the lever 59 pivoted counterclockwise from the position shown in FIG. 3 to that shown in FIGS. 4 and 5. In fact, the free end 74 of the strap 70 may be pushed through the throat of the buckle 60, with the gripping flange riding over the serrated surface or rack 76 of strap 70 and riding across the projecting parallel teeth 76A which run at right angles to the longitudinal axis of the strap. Once the strap is fully inserted to the extent of a reasonable pressure and compression of the foam liner 14 about the locale of any given leverage fastener 28, the lever 59 is rotated clockwise approximately 180° about its pivot axis A defined by rivets 61, shifting the pivot axis B of the locking pawl 64 as defined by pivot pin 65 from the front of the leverage closure 28 to the rear thereof. In reaching the pin locking notches 65, the pin 66 rides over the rear edges 67 of the lever mounting plate flanges 62B and with the compressive force exerted by the tightening of the strap and through the rotation of the lever 59, the pawl pivot pin 65 longitudinally shifts within narrow elongated slots 63 within the bifurcated arms 59, through which pin 65 passes to maintain the pawl pivot pin 65 locked to the U-shaped bracket or lever mounting plate 62.

Figure 5:
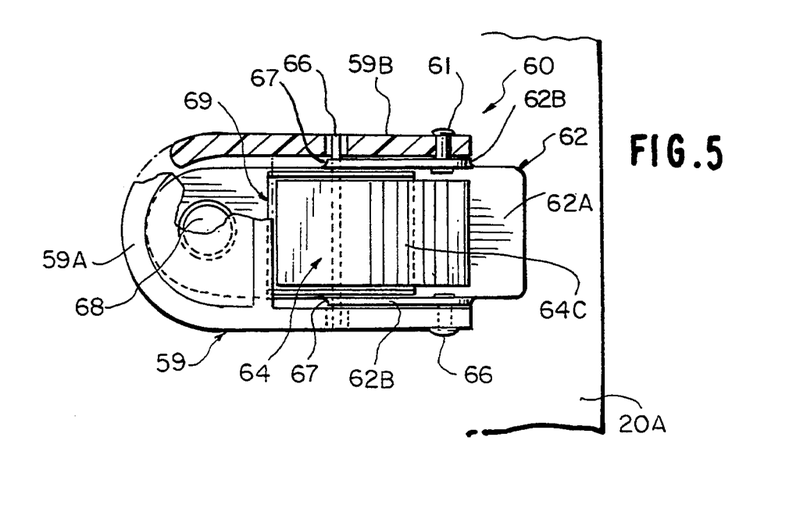
FIG. 5 is an elevational view, partially broken away, of the leverage closure of FIGS. 3 and 4.

Release is effected by the simple expedient of rotating the lever 59 counterclockwise from the locked position, FIG. 5, in the direction of the front of the boot 12 for each of the plurality of leverage closures 28.

Turning to FIG. 2, the structural makeup and features of the breathable open-pore foam liner or lining 14 may be seen in detail in FIG. 2. A unitary, molded open-pore foam unitary sheet of about ½ inch in thickness cut and edge sealed together to form a L-shaped enclosure in side elevation, which is closed on the bottom, rear and sides, but open at the front so as to freely receive the lower leg, ankle and foot of the user. The liner sides 92 wrap about the foot above the ankle, with one flap 92A underlying an opposite flap 92B. A foam interior sheet 102 is covered by a thin, woven, hook compatible sheet material outer layer 108 and a similar woven sheet material inner layer 110. A VELCRO ® hook material strip 114 carried by one flap 92B is pressed against the exterior woven outer layer 108 of flap 92A to cause the hooks 118 thereof to frictionally engage the same and to maintain the foam liner releasably locked closely about the leg of the user and conforming thereto. Similarly, by the use of a second VELCRO ® hook type fastener material strip 116 in the area of the dorsum of the foot, the hooks 118 thereof engage on the inner surface of the dorsum flap 94B, engaging the exterior woven outer layer surface of flap 94A, which is a VELCRO ® hook type compatible material, i.e., by having opposite fastener type loops. Thus, a releasable fastening system is achieved both in the area of the dorsum of the foot and the shin of the user to envelope the leg, ankle and foot of the user in a protective, breathable, soft, compressible foam envelope. Such is achieved prior to placement of the liner covered limb of the user within the boot 12 of the immobilization brace 10. While the liner 14 in FIG. 2 is illustrated as being of one piece, it may be of multiple pieces with portions sewn or otherwise edge fastened together. Further, the exposed edges of the sheet material may be sewn to reinforce the lamination between the woven inner and outer surface layers of VELCRO ® hook compatible material and the quarter inch open foam core sheet 102.

In the embodiment of FIGS. 1 and 2, in addition to the large size rivets 26 to opposite sides 20A of the boot upper 20 adjacent lower edge 40 and to the sides 35 of the boot portion 18 of the boot 12, the presence of the immobilizing rivets 58 lock the boot upper 20 in a preferred orientation at the near vertical with respect to the walking sole 16. However, as desired, the rivets 26 may provide partial immobilization, i.e., permitting some limited fore and aft angulation of the boot upper 20 with respect to the boot portion 18 and the sole, with the upper pivoting about a horizontal axis via rivets 26 to opposite sides of the immobilizing brace 10.

Full immobilization is preferable during early stages of the healing process, after the soft tissues have healed for a time, however, the prescribing physician may wish to introduce motion. To accomplish this goal, it is possible to incorporate instead of the fixedly mounted immobilizing rivets 58, a removable immobilizer bar fitted in the heel portion of the short leg walker in the embodiment of FIG. 1 having two projecting prongs which protrude through aligned dual horizontally spaced, square openings within both the boot portion 18 and the upper portion 20 of the short length leg walker or immobilization brace 10 to selectively eliminate such fore and aft motion during attachment. When removed, limited motion of the boot upper 20 is achieved, relative to the boot portion 18 and the relatively rigid walking sole 16 bonded thereto. In a preferred form, the immobilizer bar takes the shape of a rectangular plan configuration molded plastic strip of some height, and of a width so as to extend across the heel from one side of the boot 12 to the other. The immobilizer bar is fitted to the inside of the boot in the area of an overlap between the lower end of the boot upper 20 and the boot portion 18, near the top rear of that member. Two square holes, approximately 0.5 cm square may be provided at laterally spaced positions in the heel area of both the upper and the boot portion, matching 0.5 cm square pegs, approximately 1.5 cm in length, projecting outwardly of the rear surface of the molded plastic strip piece constituting the immobilizer bar proper. When fitted through the aligned holes within the boot upper and the boot portion, the immobilization bar takes the place of the rivets 58 as illustrated in the embodiment of FIG. 1. The pair of immobilizing rivets 58 on opposite sidewalls of the boot upper 20 face forwardly and rearwardly of the larger rivets 26, and constitute a triangular locking arrangement to immobilize the upper in the fore and aft direction with respect to the boot portion of the boot.

Figure 6:
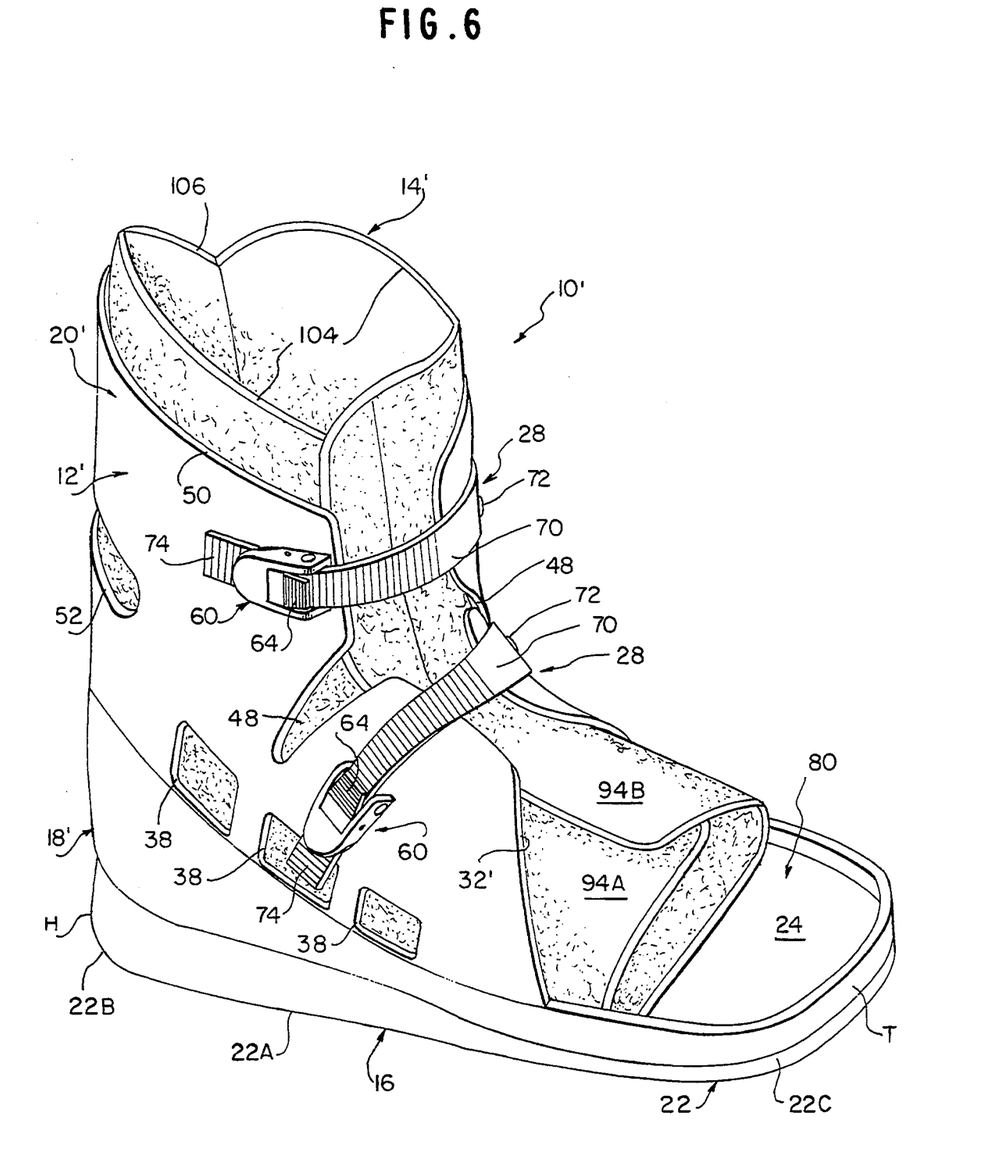
FIG. 6 is a perspective view of an immobilization brace forming a second embodiment of the invention.

Further, both with respect to the embodiment of FIGS. 1-5 inclusive and that of FIG. 6, the immobilization brace 10 and 101 may be used in combination with a single-piece, heat molded or heat and pressure molded insole, which may function as an addition to or substitute for the foam insole 24, as for example in the embodiment of FIG. 1. Such additional insole may be made of a heat moldable material sold commercially under the trademark "PLASTAZOTE TM" which, when subject to heat, will function to mold the plantar aspect of the user's foot, thereby reducing pressure on neuropathic ulcerations and other plantar lesions on the foot.

Both embodiments of the invention may be used to replace the total contact method of treating ulcerations. With this method, a cast is placed on the lower leg to immobilize the foot and ankle and the casting material is also extended down the full length of the plantar surface of the foot to help redistribute the weight off of sensitive areas. The immobilizing brace of the present invention incorporating such further insole will accomplish the same pressure relief by immobilizing the foot and ankle while the insole solely molds to the plantar aspect of the foot. Preferably, the additional insole should be both heat and pressure moldable such that it may be heated in a convection oven prior to being placed in the walker and on the upper surface of the molded unitary outer sole 22. Alternatively, an unheated insole, which may reform can be used wherein the combination of the user's body weight and body heat acts to form the insole to the plantar aspect of the foot over time.

The present invention in both embodiments preferably employs decompression pads 86 removably fixed to opposite exterior surfaces of liner 14, FIGS. 2, as an example. The pads 86 in this embodiment are of L-shape having a long vertical portion 82 integral with a shorter length horizontal portion 88. The pads applied about the ankle bone are of a near rigid open pore foam liner 14 with a hook type surface layer on one face 84 which readily detachably fastens to the hook compatible sheet material 108 covering the exterior surface of the liner 14. The vertical portion of the L is placed behind the ankle bore or malleoli and the short horizontal portion below the ankle bone.

Alternatively, the compression pad may be formed of a round or square hollow plastic pouch, sealed along its edges and filled with a gel or a liquid foam or paste such as that sold under the trademark FLOAM TM by Genesis Composites, Inc. of Salt Lake City, Utah. Such pads of gel or FLOAM TM are centered on the ankle bone, extending to both sides thereof.

Further, while in the first embodiment of the invention the buckles and straps are illustrated and described as being riveted, they may be alternatively bolted onto the exterior surfaces of the boot upper 20 and the boot portion 18 of boot 12, along with one end of the straps 70 which span across the open front of the boot 12. Thus, either or both the buckles and the straps may be mounted for selective removal. The employment of interchangeable buckles and straps permits the physician to customize the immobilization brace 10 and that at 10' in the alternative embodiment, so that an adjustable compression force closure may be effected either to the left or right.

Turning to FIG. 6, modified, low top short length leg walker or immobilization brace 10' incorporates all of the features of the first embodiment with the exception that the boot 12' thereof is of a height so as to extend just above the ankle of the user. Further, the boot 12' is molded as a single piece and applied to the walking sole 16 in the same manner as the first embodiment. Like elements bear like numerical designations within FIG. 6 to those of the first embodiment within FIGS. 1–5 inclusive. This ankle high embodiment is different from the full length embodiment of FIG. 1, primarily in terms of its height. Further, the boot 12' does not extend forwardly down the forefoot to the same extent as in the first embodiment, being considerably shortened and exposing a greater surface area of the liner 14 wrapped about the dorsum of the foot.

The embodiment of FIG. 6 is fully immobilizing and cannot be modified as in the first embodiment. The walking sole 16 is essentially identical to that of the first embodiment, is provided with the same bottom surface portions, a long central flat portion 22A, terminating in the direction of heel H in an upwardly and rearwardly rounded portion 22B, and forwardly in a gently curved, upwardly rising surface portion 22C to toe T. Interiorly, within a recessed portion of the molded plastic boot portion 18', there is provided a foam insole indicated in dotted lines at 24 which may be identical to that of the first embodiment. The open toed aspect of the boot 12' and that of the modified breathable foam open pore liner 14' is carried over in this embodiment, although a greater portion of the foot content 94 of the liner is exposed. The nearly vertical front edge of the boot 12' is much closer to the heel H of the immobilization brace 10' than in the brace 10. In similar fashion to the first embodiment, the boot 12' is provided with three trapezoidal shaped, rearwardly and upwardly directed, slightly spaced ventilation ports or openings 38. Further, a frontal V-notch 48 is provided within the frontal edge of boot 12', with the boot portion 18' and the boot upper 20' being integrally molded of the same polyurethane material and thus of the same flexibility. A single V-notch 48 separates the two adjustable fasteners or closures 28, those elements being identical to the adjustable closure system of the first embodiment. The boot 12' is provided with a single arcuate ventilation port or slot 52 across the rear of the boot at some distance above the heel H. The upper edge 50 of the boot upper 20', in similar fashion to the first embodiment, is sloped upwardly and rearwardly so that the top of the boot 12' is higher at the rear than that at the open front, and further the side edges 104 and the rear edge 106 of the open pore foam liner 14' conforms to the configuration of the boot upper 20', but being slightly higher.

The breathable open pore foam liner 14' therefore extends slightly above the enveloping outer boot 12'. In the low top immobilizing brace 10', the shoe upper 20' terminates just above the malleoli. It has been found that in many cases, particularly after forefoot surgery or when treating the diabetic or ischemic foot, the additional height of the high top brace 10, FIG. 1, is not necessary. Further, the exterior boot 12' does not extend as far down the forefoot in order not to place any pressure on the sides of the metatarso-phalangeal joint for most of the forefoot surgery performed. By shortening the length of the boot down the foot, one guarantees that there will be no undue pressure on the forefoot that would cause discomfort or displacement of the soft tissues or bones of the forefoot after reconstructive surgery.

While the invention has been described with respect to several embodiments and while changes and modifications have been discussed to some degree, it should be apparent that various other changes may be made to the immobilization brace without departing from the scope of the invention. While the single part or two-part injection-molded boot is described as formed of polyurethane, it should be readily apparent that other plastics may be employed, providing the requisite strength and duramoter hardness so that the front open boot can conform to the limb of the user with uniform general compression over the complete surface area of the limb so encompassed. Further, the makeup of the composition of the rocker sole 16, the foam insole 24 and the open pore foam liner may be varied, while retaining the porosity and breathability of the liner and the ventilation access through the ports within the molded plastic boot. Further, while in the embodiments illustrated and described, there is a recess within the boot portion 18' fixedly bonded to the sole 16 to which is hingedly coupled the boot upper 12 in the embodiment of FIG. 1 and which is carried over to the second embodiment of FIG. 6, which recess is partially defined by a protective vertical rim about the forefoot area of the immobilization brace 10 and that at 10', it is possible that the foam insole 24, or even a further insole or insert of a heat and/or pressure moldable sheet material may fill or nearly fill that recess without departing from the spirit and scope of the invention. The invention, therefore, is limited solely by the claims appended hereto.

What is claimed is:

1. A lower leg, ankle and foot immobilization brace preventing torsion of the leg, ankle and foot of the user while preventing dorsiflexion and plantar flexion of an ankle joint comprising:

a generally rigid walking sole of minimal thickness provided with a rocker bottom surface having an extensive flat central bottom surface portion to permit the user to stand at about the same thickness as a conventional shoe sole and a contoured footbed, a semi-flexible boot portion fixedly attached to the top of the walker sole having a rounded heel counter for achieving a good fit of the limb of the user with increased stability and comfort, a shock absorbing foam insole constituting a pad for the plantar surface of the user's foot mounted to said foot portions and overlying the same, a semi-flexible molded plastic boot upper extending vertically from the boot portion having a rear wall and a pair of integral opposite sidewalls, being open at the front, merging with sidewalls of the boot portion and forming an open toed structure above the foam insole, a plurality of ventilation ports within the boot portion and at least one ventilation port within the boot upper, an open toed, open pore breathable foam liner surrounding the lower foot, ankle and dorsum of the user and terminating at the forefoot in the area of the metatarso-phalangeal joint, and leverage closure means spanning said open front of said molded plastic boot for applying general and focal compression to said foam liner encased limb of the user over the lower leg, ankle and dorsum thereby minimizing edema induced swelling over the full extent of the boot.

2. The immobilization brace as claimed in claim 1, wherein said boot sides have front edges, and said boot further comprising notches within said front edges of the sides of said molded plastic boot forming independent spaced, flexible areas, and wherein said leverage closure means are mounted respectively to said spaced flexible areas of said boot to facilitate the application of both the focal and general compression to the foam liner encased limb of the user.

3. The immobilization brace as claimed in claim 1, wherein said boot portion is of general U-shape vertical section having a recess over the complete length of the immobilizing brace for encasing the heel and foot of the user, defined partially by a vertical rim about the open toed portion of said boot.

4. The immobilization brace as claimed in claim 1, wherein said sole and said boot portion narrows from heel to toe in front of the ankle, widens in the vicinity of the metatarso-phalangeal joint and further narrows slightly at the toe of the immobilization brace.

5. The immobilization brace as claimed in claim 1, wherein said flexible molded plastic boot is a two-part structure with said boot portion being upwardly open, rising vertically from said sole and integral with said boot upper, and said boot upper is vertically elongated and of generally C-shaped horizontal cross-section, said boot comprises means for pivotably coupling opposite sides of a lower end of the boot upper to respective opposite sides of the boot portion above the sole for pivoting about a horizontal axis, and wherein said immobilization brace further comprises means for preventing fore and aft rotation of the boot upper about said horizontal axis of said pivotably coupling means.

6. The immobilization brace as claimed in claim 5, wherein said means for preventing rotation of said boot upper about the means pivotably coupling the boot upper to the boot portion comprises at least one rivet coupling the boot upper to the boot portion at a point remote from said coupling means.

7. The immobilization brace as claimed in claim 5, wherein front edges of the sides of said boot portion include a V-notch defining separate, spaced flexible areas of said boot portion, across which areas a pair of said leverage closures span respectively, and wherein the front edges of the sides of the boot upper at said open front include a plurality of V-notches forming separate, spaced areas of increased flexibility, each of which has a respective one of said leverage closures spanning across the same, such that said leverage closures are generally uniformly spaced over the extent of the foot, ankle and anterior portion of the boot.

8. The immobilization brace as claimed in claim 1, wherein said breathable foam liner comprises a hook type compatible fastener external layer, and wherein said liner includes overlapping side flaps, one of said side flaps having a strip of hook type fastener material on an external surface thereof facing and engaging the hook type compatible material layer of an opposite side flap of the liner thereby maintaining the liner closely wrapped about the limb of the user, and wherein said hook type compatible material is porous to facilitate ventilation of the limb of the user through said ventilation ports of said boot.

9. The immobilization brace as claimed in claim 1, further comprising decompression pads mounted to an exterior surface of the liner to opposite sides thereof facing the limb of the user and positioned about the ankle bone of the user to reduce fluid accumulation around the ankle bone and prevent swelling in the presence of edema.

10. The immobilization brace as claimed in claim 9, wherein said decompression pads comprise a strip of hook type fastener material on the exterior surface thereof facing said open pore foam liner and engaged with said hook type compatible material on the exterior surface layer of the liner.

11. The immobilization brace as claimed in claim 10, wherein said decompression pad comprises one mass of the group consisting of a dense solid foam, a sealed gel mass, and a sealed liquid foam.

12. The immobilization brace as claimed in claim 9, wherein said decompressions are of L-shaped plan configuration including a generally vertical portion behind the ankle bone of the user and an integral, generally horizontal portion beneath said ankle bone.

13. The immobilization brace as claimed in claim 1, wherein said leverage closure means comprises a plurality of serrated straps fixed at one end to one side of said boot and of a length spanning across the open end of said boot and overlying the opposite side thereof, a plurality of buckles aligned with said straps and fixed respectively to the opposite sides of said boot at levels corresponding to said straps, said buckles each include a pivotable lever mounted for rotation at one end about an axis at right angles to longitudinal axes of the straps and pivotable through approximately 180°, spring biased pawls pivotably mounted to said pivotable levers at a position outboard of the pivot connection between the levers and said boot and commonly pivoting guide plates forming with said pawls throats receiving the free ends of said straps, and wherein said pawls each include a flange engageable with a serrated surface of said strap for locking said strap to said pivotable levers such that said levers upon rotation cause opposite sides of said boot to move towards each other with serrations of said free ends of the straps engaged by said pawls to compress the liner encased limb of the user.

14. The immobilization brace as claimed in claim 13, further comprising means carried by said buckle for latching said lever in a position pivoted away from the opposite side of the boot such that said straps are under maximum tension.

15. The immobilization brace as claimed in claim 14, wherein said buckles each include a U-shaped lever mounting plate fixed to an exterior surface of the boot adjacent one side edge thereof, said mounting plate comprises laterally spaced sidewalls having rear edges which include a locking notch, and wherein said spring biased pawls are pivotably mounted to said arm by a pivot pin, and wherein the levers are pivoted at one end to said sidewalls of said U-shaped lever mounting plate intermediate the ends thereof, such that the pivot pins pivotably coupling the spring biased pawls to the rotatable levers move into said locking notches of said mounting plate sidewalls to lock the levers in latched position.

* * * * *